(12) United States Patent
Masaki (10) Patent No.: US 8,789,948 B2
(45) Date of Patent: Jul. 29, 2014

(54) CONTROL APPARATUS, CONTROL METHOD, AND OPHTHALMOLOGIC APPARATUS INCLUDING THE CONTROL APPARATUS

(71) Applicant: Canon Kabushiki Kaisha, Tokyo (JP)

(72) Inventor: Toshifumi Masaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/845,528

(22) Filed: Mar. 18, 2013

(65) Prior Publication Data

US 2013/0215389 A1    Aug. 22, 2013

Related U.S. Application Data

(63) Continuation of application No. 13/210,413, filed on Aug. 16, 2011, now Pat. No. 8,425,038.

(30) Foreign Application Priority Data

Aug. 31, 2010   (JP) ................................. 2010-194641

(51) Int. Cl.
   *A61B 3/14*   (2006.01)
   *A61B 3/10*   (2006.01)

(52) U.S. Cl.
   USPC .......................................... 351/206; 351/205

(58) Field of Classification Search
   USPC ................................................. 351/200–246
   See application file for complete search history.

(56) References Cited

U.S. PATENT DOCUMENTS

| 4,577,141 A | 3/1986 | Saiki et al. |
|---|---|---|
| 4,695,137 A | 9/1987 | Jorgens et al. |
| 5,352,889 A | 10/1994 | Fujieda et al. |
| 5,822,034 A | 10/1998 | Shimashita et al. |
| 5,886,684 A | 3/1999 | Miura et al. |
| 7,654,670 B2 | 2/2010 | Mimura |
| 8,425,038 B2 * | 4/2013 | Masaki ......................... 351/206 |
| 2005/0254360 A1 * | 11/2005 | Sameshima et al. ....... 369/44.23 |
| 2009/0079939 A1 | 3/2009 | Mimura |
| 2011/0187739 A1 * | 8/2011 | Takagi ........................... 345/619 |

FOREIGN PATENT DOCUMENTS

| CN | 1866366 A | 11/2006 |
|---|---|---|
| JP | 5-317250 A | 12/1993 |

(Continued)

OTHER PUBLICATIONS

Dec. 22, 2011 European Search Report in European Patent Appln. No. 11178459.1.

(Continued)

*Primary Examiner* — Mohammed Hasan
(74) *Attorney, Agent, or Firm* — Fitzpatrick, Cella, Harper & Scinto (57) ABSTRACT

In an ophthalmologic apparatus in which a head part is moved at a speed according to a rotation speed of a rotational part of a joystick, in order to enable a moving amount of the head part to correspond to a rotation amount even when the rotation speed becomes higher, the rotation speed of the joystick is detected at predetermined intervals, and when a current rotation speed (count of an encoder during a predetermined period) is lower than a previous rotation speed, a speed obtained by subtracting a predetermined value from the previous rotation speed is compared to the current rotation speed. Then, a higher speed is set as the current rotation speed, and the head part is moved at the speed corresponding to the current rotation speed.

19 Claims, 6 Drawing Sheets

(56) References Cited

FOREIGN PATENT DOCUMENTS

| | | |
|---|---|---|
| JP | 06-014882 A | 1/1994 |
| JP | 3237907 B2 | 12/2001 |
| JP | 2002-136480 A | 5/2002 |
| KR | 10-2009-0024097 A | 3/2009 |

OTHER PUBLICATIONS

May 9, 2012 European Search Report in European Patent Appln. No. 11178459.1.

Apr. 17, 2014 Chinese Official Action in Chinese Patent Appln. No. 201110252513.8.

* cited by examiner

CONTROL APPARATUS, CONTROL METHOD, AND OPHTHALMOLOGIC APPARATUS INCLUDING THE CONTROL APPARATUS

This application is a continuation of application Ser. No. 13/210,413 filed Aug. 16, 2011 now U.S. Pat. No. 8,425,038 B2.

BACKGROUND OF THE INVENTION

1. Field of the Invention

The present invention relates to a control apparatus including a joystick for controlling a control target, a control method, and an ophthalmologic apparatus including the control apparatus to electrically perform vertical movement of an optical system as the control target, for imaging and measurement of an eye to be inspected.

2. Description of the Related Art

As a configuration for controlling a control target with a joystick, a fundus camera including a joystick to control an optical system may be taken as an example. In a conventional ophthalmologic apparatus such as the fundus camera, the joystick is used for positional alignment between the optical system of the apparatus and an eye to be inspected. In such an apparatus, the joystick is inclined to perform back-and-forth movement and lateral movement, while the joystick is rotated to perform vertical movement. More specifically, there are known an apparatus in which the optical system is vertically moved manually by rotating a feed screw of a vertical movement drive mechanism of the optical system in combination with a belt, a gear, and the like, and an apparatus in which the optical system is vertically moved electrically. As the apparatus in which the optical system is vertically moved electrically, there is known an apparatus in which a motor is controlled so that the optical system is moved at a speed proportional to a rotation speed of the joystick (see Japanese Patent Application Laid-Open No. H05-317250). Further, there is known an apparatus in which the motor is controlled so that the optical system is moved at a speed nonlinear with respect to the rotation speed of the joystick, and as the joystick is rotated more quickly, the optical system can be moved at higher speed (see Japanese Patent No. 3,237,907).

However, in each of the apparatuses described in Japanese Patent Application Laid-Open No. H05-317250 and Japanese Patent No. 3,237,907, the rotation speed of the motor has an upper limit, and hence, when the rotation speed of the joystick becomes a fixed value or larger, the moving speed reaches to the upper limit though the joystick is rotated even quickly. Therefore, there arises a problem that the moving amount conversely decreases when the joystick is rotated quickly. There is a method in which a motor having a higher upper limit of the rotation speed is employed to control the motor to track the rotation speed of the joystick, but in this case, the high-performance motor is generally large in size and expensive. Further, a high-output power source is necessary to drive the motor, resulting in a problem that the apparatus becomes expensive and large in size.

SUMMARY OF THE INVENTION

The present invention relates to an apparatus, including: a joystick for controlling a control target; a detection unit for repeatedly detecting a rotation amount of a rotational member provided to the joystick; and a control unit for outputting a control value corresponding to the rotation amount according to the detection, in which when a decrease in the rotation amount, in which an amount of decrease in the control value per unit time exceeds a threshold value, has occurred, the control unit restricts the amount of decrease in the control value per unit time to a value that avoids exceeding the threshold value.

Further, the present invention relates to a control method for an apparatus including a joystick for controlling a control target, the control method including: repeatedly detecting a rotation amount of a rotational member provided to the joystick; outputting a control value corresponding to the rotation amount according to the detecting; determining whether or not a decrease in the rotation amount, in which an amount of decrease in the control value per unit time exceeds a threshold value, has occurred; outputting, when it is determined that the decrease in the rotation amount does not occur, the control value so that a sum of the control values to be output becomes a first value corresponding to a sum of the detected rotation amounts; and restricting, when it is determined that the decrease in the rotation amount has occurred, the amount of decrease in the control value per unit time to a value that avoids exceeding the threshold value to output the control value so that the sum of the control values becomes larger than the first value.

In addition, the present invention relates to an ophthalmologic apparatus including: detection means for detecting a rotation speed and a rotation direction of a rotational member provided to a joystick at predetermined sampling intervals; drive means for electrically performing vertical movement of an optical system for imaging, observation, and measurement of an eye to be inspected; control means for controlling the drive means at a speed and in a direction respectively corresponding to the rotation speed and the rotation direction of the rotational member that are detected at a current sampling by the detection means; storage means for storing the rotation speed and the rotation direction of the rotational member that are detected by the detection means; and subtraction means for calculating, when the rotation direction at a previous sampling that is stored in the storage means and the rotation direction at the current sampling are the same, or when the rotation speed is zero, a rotation speed obtained by subtracting a predetermined value from the rotation speed at the previous sampling that is stored in the storage means, in which the control means compares the rotation speed obtained through the subtraction to the rotation speed at the current sampling, and sets a higher speed as the rotation speed at the current sampling to be used for controlling the drive means.

According to the present invention, the rotation speed of the rotational part of the joystick is detected at the predetermined intervals, and when the current rotation speed is lower than the previous rotation speed, the speed obtained by subtracting the predetermined value from the previous rotation speed is compared to the current rotation speed. Then, a higher speed is set as the current rotation speed, and the head part is moved at the speed corresponding to the current rotation speed. Such a configuration can solve the problem inherent in the conventional case that, when the rotation speed is high while the rotation amount of the rotational part of the joystick is the same, the moving amount of the head part conversely decreases. Accordingly, operability can be improved. Further, even in a case where an inexpensive, small-size motor and a low-output power source are used, the motor can be controlled to track the rotation amount of the joystick, and thus an inexpensive, small-size apparatus can be provided.

Further features of the present invention will become apparent from the following description of exemplary embodiments with reference to the attached drawings.

BRIEF DESCRIPTION OF THE DRAWINGS

FIG. 6 is comprised of FIGS. 6A and 6B showing flow charts according to a first embodiment of the present invention.

DESCRIPTION OF THE EMBODIMENTS

First Embodiment

The present invention is described in detail based on exemplary embodiments illustrated in FIGS. 1 to 6.

Figure 1:
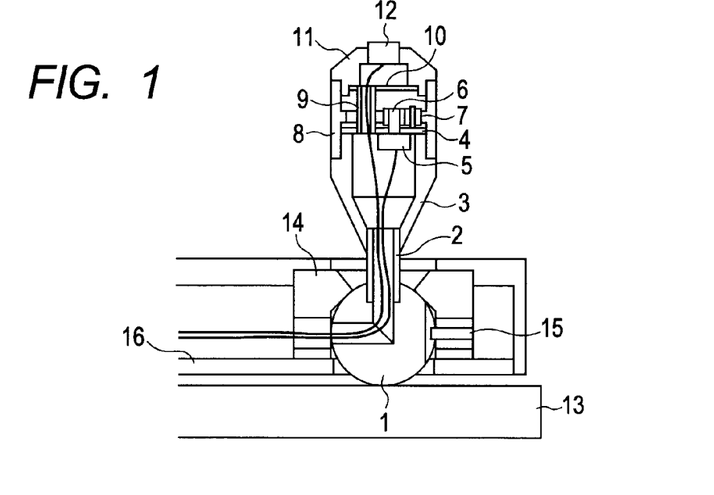
FIG. 1 is a configuration diagram of a joystick.

FIG. 1 is a schematic configuration diagram of a joystick according to a first embodiment of the present invention. A ball part 1 has a shaft 2 fixed thereto. The shaft 2 has a frame 3 of the joystick fixed thereto.

A plate 4 is fixed to the frame 3, and a rotary encoder 5 and a support column 9 are fixed to the plate 4. An upper cover 11 of the joystick has a switch 12 fixed thereto, and the switch 12 is used for starting imaging, measurement, and the like. The upper cover 11 is fixed to the support column 9 through the intermediation of a plate 10. A rotational member 8 is fitted between the frame 3 and the upper cover 11 so as to freely rotate. The rotational member 8 has a gear 7 formed inside. When the rotational member 8 rotates, the gear 7 and a gear 6 fixed to a shaft of the rotary encoder 5 rotate in association, and as a result, the shaft of the rotary encoder 5 rotates, thereby detecting a rotation amount of the rotational member 8. The ball 1 is housed in a ball housing 14 fixed to a stage frame 16 and rolls on a base frame 13 when the joystick is inclined, and therefore a stage part is finely movable horizontally. In a case of rough movement, when a fixed force or more is applied to the joystick, the ball 1 and the base frame 13 start to slide, and therefore the stage part is greatly movable horizontally. A pin 15 serves as a stop for rotation of the entire joystick, and is inserted into a slit provided to the ball 1. Electric wires extending from the switch 12 and the rotary encoder 5 pass through the support column 9 and the shaft 2, and further pass through a hole in the ball 1 so as to be connected to an electric equipment part (not shown).

Figure 2:
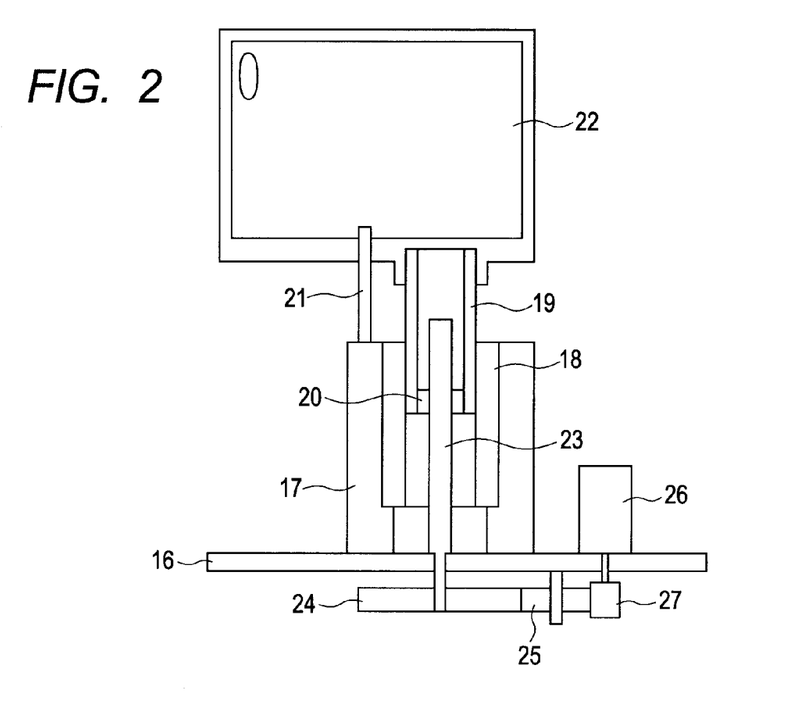
FIG. 2 is a configuration diagram of a vertical movement mechanism for a head part.

FIG. 2 is a schematic configuration diagram of a vertical movement mechanism for a head part. A support column 17 is fixed to the stage frame 16, and a bearing 18 is inserted and fixed inside the support column 17. A vertical movement shaft 19 is inserted inside the bearing 18, and is movable vertically. A head part 22 is fixed to the upper portion of the vertical movement shaft 19. Various kinds of optical system to be used for carrying out imaging, observation, and measurement of an eye to be inspected are built into the head part 22 as an ophthalmologic apparatus, but details thereof are not illustrated because there is no direct relevance to the present invention. A nut 20 threaded into a female screw is fixed to the lower portion of the vertical movement shaft 19. A feed screw 23 is coupled to the inner side of the nut 20, and a gear 24 is fixed to the lower portion of the feed screw 23. A motor 26 fixed to the stage frame 16 is a DC motor, and a pinion gear 27 is fixed to a rotation shaft thereof. When the motor 26 is rotated, the rotation is transmitted to the gear 24 through a deceleration gear 25 coupled to the pinion gear 27. When the gear 24 rotates, the feed screw 23 rotates, and the nut 20 coupled to the feed screw 23 and the vertical movement shaft 19 move accordingly. Therefore, the head part 22 is movable vertically.

A shaft 21 fixed to the support column 17 is used for preventing the rotation of the head part 22, and passes through the head part 22.

Figure 3:
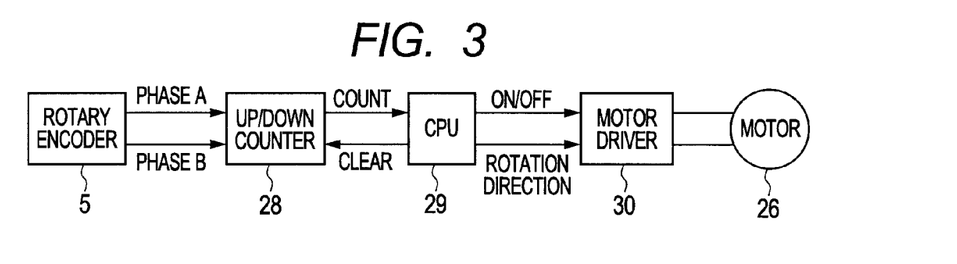
FIG. 3 is a block diagram of electrical components.

FIG. 3 is a block diagram of electrical components. The rotary encoder 5 is a general two-phase encoder, and transmits pulse signals of phase A and phase B proportional to the rotation amount to an up/down counter 28.

The up/down counter 28 is capable of counting in a positive direction or in a negative direction based on the number of edges and the phase of the pulse signals of phase A and phase B. In the present invention, the up/down counter 28 counts in the positive direction when the rotational member 8 of the joystick rotates clockwise, and counts in the negative direction when the rotational member 8 rotates counterclockwise. Hence, the rotation amount and the rotation direction of the rotational member 8 of the joystick are detectable. A CPU 29 reads a value counted by the up/down counter 28 every predetermined cycle (for example, every 20 msec), stores the value in an internal memory, and sends a clear signal to the up/down counter 28 to clear the counter. The components exemplified by the rotary encoder 5, the up/down counter 28, and the CPU 29 function as detection means for detecting the rotation speed and the rotation direction of the rotational member 8 every predetermined cycle, that is, at predetermined sampling intervals. Further, those components may be defined as a detection unit for repeatedly detecting the rotation amount of the rotational member provided to the joystick. In this case, it is preferred that the pattern of repetition may be set variously as necessary.

A motor driver 30 for driving the motor 26 controls forward/reverse rotation and ON/OFF of the motor based on a rotation direction signal and an ON/OFF signal transmitted from a port of the CPU 29. When the ON/OFF signal is set to a Hi level, power is supplied to the motor 26, and when the ON/OFF signal is set to a Low level, the power of the motor 26 is turned off.

When the rotation direction signal is set to a Hi level, the motor 26 performs forward rotation, and when the rotation direction signal is set to a Low level, the motor performs reverse rotation.

Thus, it may be considered that the CPU 29 constitutes a control unit for outputting, to the motor driver 30, a control value corresponding to the detected rotation amount or alternatively the detected rotation direction and rotation speed.

Further, the rotation speed of the motor 26 is changed by supplying a PWM signal to the ON/OFF signal for the motor driver 30. For example, when a drive voltage of the motor is 12 V, an effective voltage to be applied to the motor is substantially a voltage expressed by 12×(duty cycle) (V). The duty cycle is expressed by (ON period)/((ON period)+(OFF period)), and when the ON period equals the OFF period, the effective voltage to be applied to the motor is 6 V. In a case of changing the voltage to be applied to the motor 26 as described in the embodiments below, such a change is regarded as the change of the effective voltage under PWM control.

Figure 4:
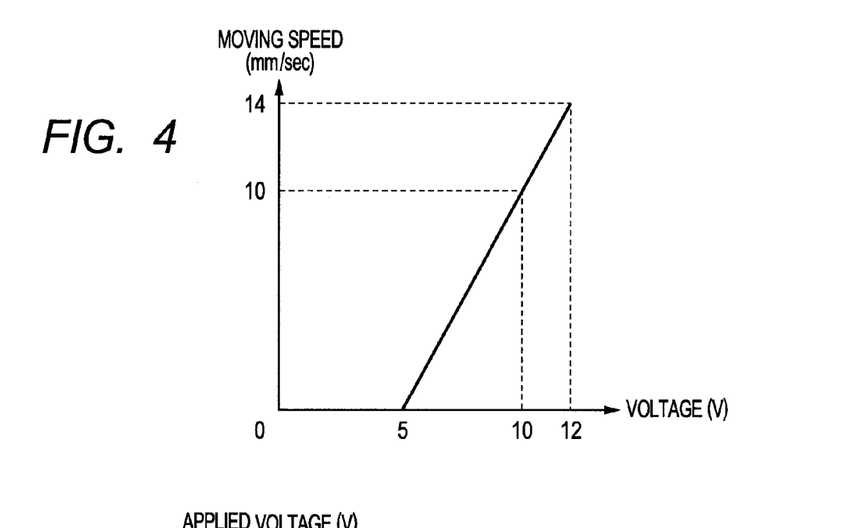
FIG. 4 is a graph showing a relationship between a voltage of a motor and a head moving speed.

FIG. 4 is a graph showing a relationship between an applied voltage of the motor and a moving speed of the head part 22 according to this embodiment. Due to an influence of friction of a drive system or the like, when a voltage of a fixed value or larger is applied, the motor 26 starts to rotate and thereafter the motor 26 rotates at a rotation speed substantially proportional to the applied voltage, thereby moving the head part 22. In this embodiment, the rotation start voltage is 5 V and the moving speed of the head part 22 at the maximum applied voltage 12 V is 14 mm/sec, but needless to say, those numerals vary depending on the motor to be used, the weight of the head part, and the like, and hence differ among apparatuses.

Figure 5:
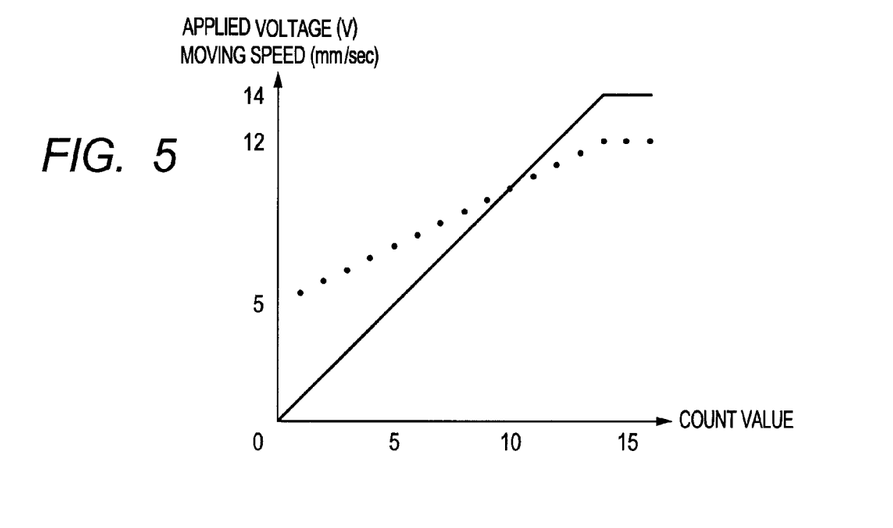
FIG. 5 is a graph showing a relationship between a count value of a rotary encoder and the voltage of the motor, and between the count value of the rotary encoder and the head moving speed.

FIG. 5 is a graph showing a correspondence between a count value of the rotary encoder 5 per sampling period and the moving speed of the head part 22, and between the count value of the rotary encoder 5 and the applied voltage of the motor 26. The solid line indicates the moving speed of the head part, and the black spots indicate the applied voltage of the motor 26. The count value of the rotary encoder 5 per unit time is proportional to the rotation speed of the rotational member 8, and hence the applied voltage is controlled so that the count value has a proportional relationship with the moving speed of the head part 22. For example, a voltage of 7.5 V is applied to the motor 26 based on the relationship of FIG. 4 so that when the count value is 5, the moving speed of the head part 22 is 5 mm/sec.

When the count value is 14, the applied voltage of the motor 26 reaches to 12 V, which is an upper limit voltage of the motor 26, and the moving speed of the head part at this time is 14 mm/sec. When the count value is 15 or larger, the upper limit voltage of 12 V is applied to the motor 26. When the count value is 15 or larger, the moving speed of the head part cannot be increased by the motor 26, and thus this count value corresponds to an upper limit rotation speed according to the present invention.

As described above, the head part 22 serving as the above-mentioned optical system is vertically driven by the motor 26 serving as drive means. Further, the CPU 29 functions as control means for controlling the moving speed of the head part 22 by the motor 26, and uses information on the rotation speed and the rotation direction obtained from the rotational member 8 of the joystick as a command signal for controlling the motor 26. Note that, this embodiment exemplifies the motor 26 as the drive means for electrically driving a target object, but the drive means of the present invention is not limited to the motor as long as the drive means is configured to operate electrically and control the operation amount.

Figures 6, 6A:
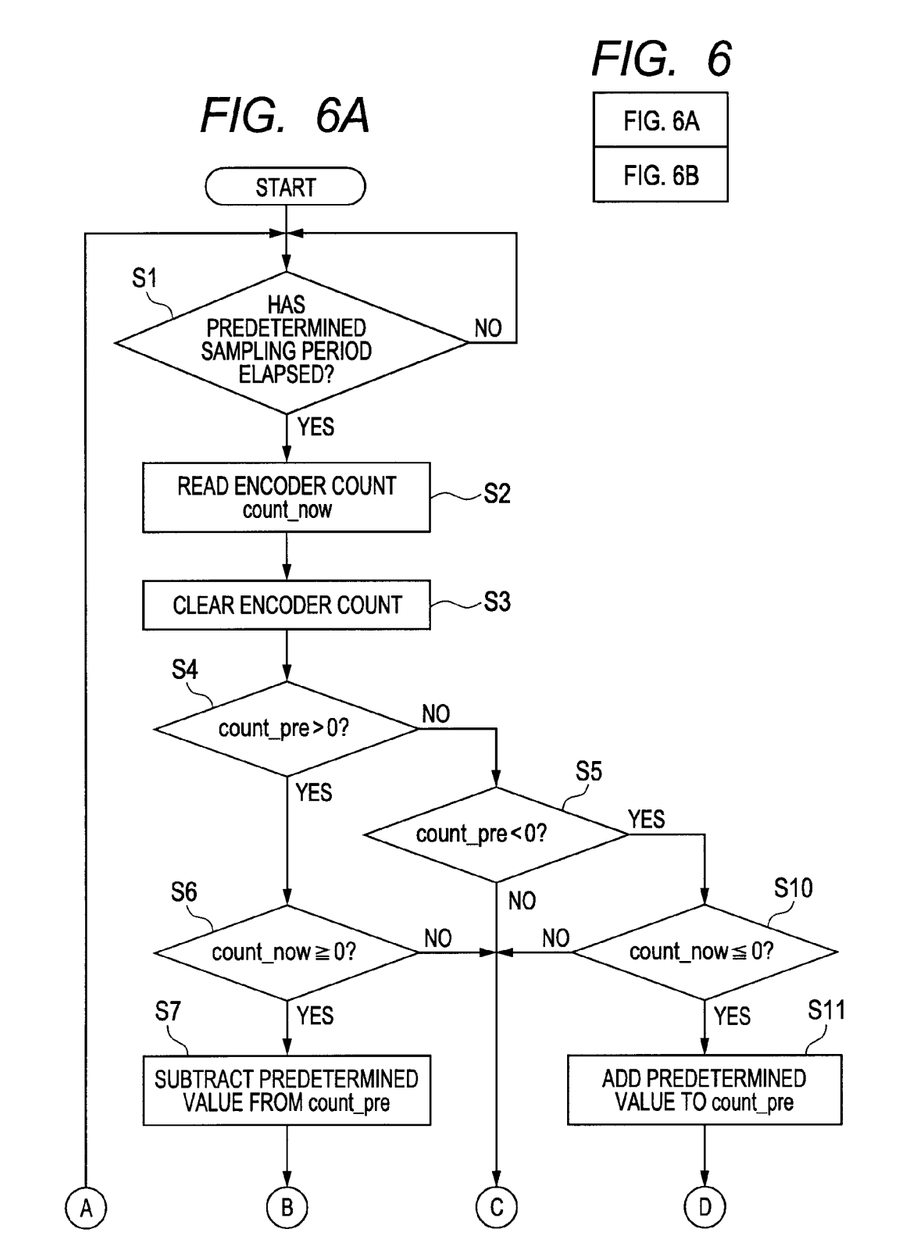
Figure 6B:
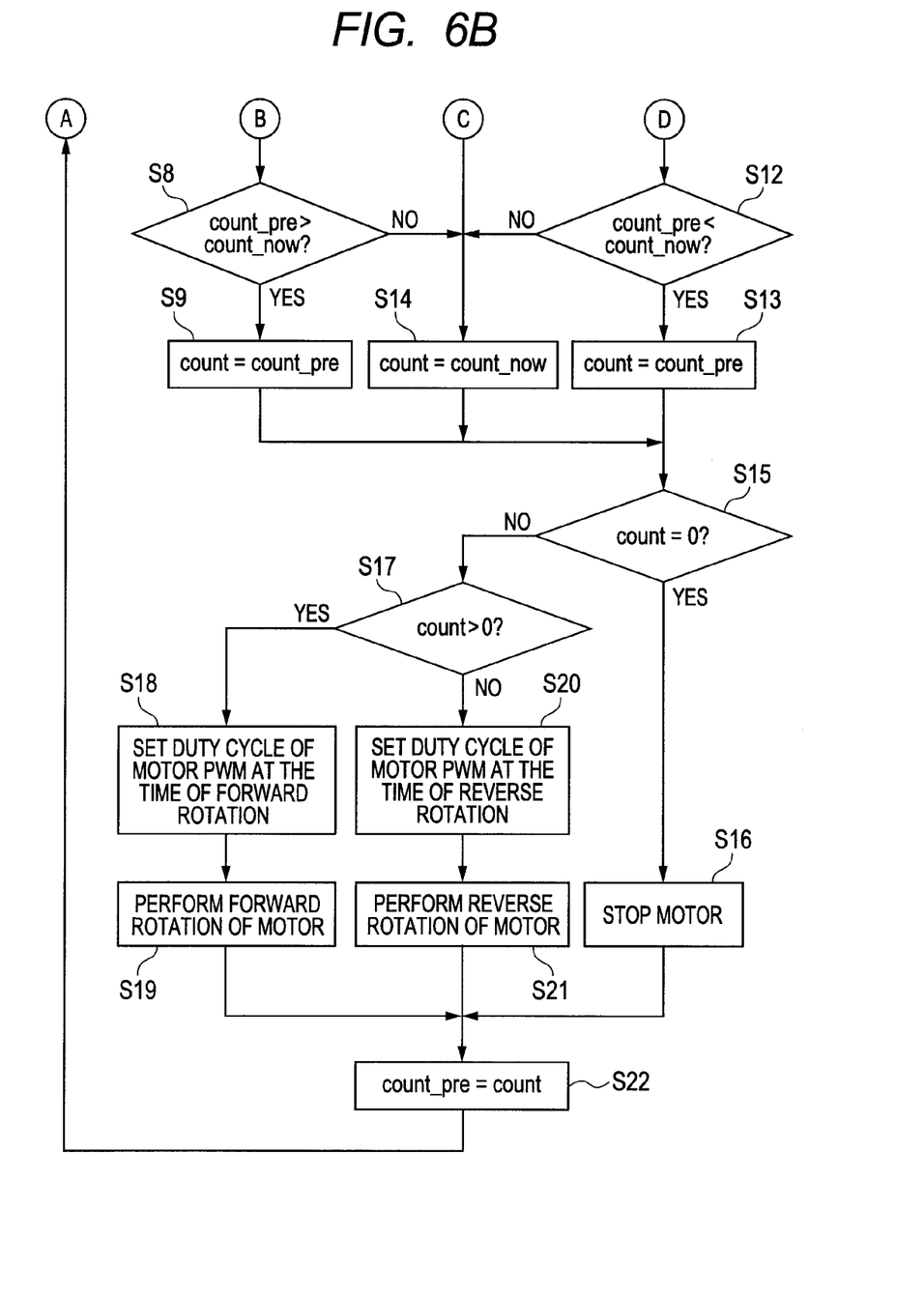

Referring to flow charts of FIGS. 6A and 6B, a movement control method for the head part 22 according to the rotation of the rotational member 8 of the joystick in the ophthalmologic apparatus having the above-mentioned configuration is described.

First, in Step 1, it is determined whether or not a predetermined sampling period or interval has elapsed.

After the predetermined sampling period has elapsed, the processing proceeds to Step 2, in which the CPU 29 reads the count value of the up/down counter 28 and stores the count value in the internal memory as a current count value count_now. Note that, the internal memory corresponds to storage means according to the present invention. The CPU 29 reads a positive value when the rotational member 8 of the joystick rotates clockwise, a negative value when the rotational member 8 rotates counterclockwise, and 0 when the rotational member 8 is being stopped. Because the rotation amount of the rotational member 8 per unit time is detected, the count value corresponds to the rotation speed of the rotational member 8.

In Step 3, the up/down counter 28 is cleared. In Step 4, when a previous count value count_pre stored in the storage means of the CPU 29 is larger than 0, the processing proceeds to Step 6, while when the previous count value count_pre is equal to or smaller than 0, the processing proceeds to Step 5. In Step 5, when the previous count value count_pre is smaller than 0, the processing proceeds to Step 10, while when the previous count value count_pre is 0, the processing proceeds to Step 14.

In Steps 4 and 5, it is determined which of the forward rotation, the reverse rotation, and the stop corresponds to the rotation state of the joystick in a period from the previous sampling until the current sampling. Here, the previous sampling and the current sampling may be performed with a specific time interval set therebetween, and accordingly, in the present invention, it is preferred that a first timing and a second timing be defined as the timing of the previous sampling and the timing of the current sampling, respectively.

In Step 6, when the current count value count_now is equal to or larger than 0, the processing proceeds to Step 7, while in the other case, the processing proceeds to Step 14. In Step 7, a predetermined value is subtracted from the previous count value count_pre, and in Step 8, the previous count value count_pre after the subtraction is compared to the current count value count_now. When the previous count value count_pre is larger, the processing proceeds to Step 9, while in the other case, the processing proceeds to Step 14. Note that, the operation of this subtraction or subtraction to be carried out subsequently is carried out by a component of the CPU 29 which is defined as subtraction means according to the present invention. Further, the above-mentioned operation is considered as determination of whether or not a decrease in rotation amount, in which an amount of decrease per unit time in control value obtained by the CPU 29 exceeds a threshold value, has occurred. In this case, it is considered that the CPU 29 also serves as a determination unit for performing the above-mentioned determination operation.

In Step 10, when the current count value count_now is equal to or smaller than 0, the processing proceeds to Step 11, while in the other case, the processing proceeds to Step 14. In Step 11, a predetermined value is added to the previous count value count_pre, and in Step 12, the previous count value count_pre after the adding is compared to the current count value count_now. When the previous count value count_pre is smaller, the processing proceeds to Step 13, while in the other case, the processing proceeds to Step 14.

In Steps 9 and 13, the previous count value count_pre is used as a current count value "count", while in Step 14, the current count value count_now is used as the current count value "count".

In Steps 6 to 14, when the rotation direction of the rotational member 8 at the previous sampling and the rotation direction of the rotational member 8 at the current sampling are the same, or when the rotational member 8 is being stopped, a value obtained by subtracting a predetermined value from the absolute value of the previous count value is compared to the absolute value of the current count value, and a larger value is set as the count value "count" for driving the current motor 26.

In Step 15, when the count value "count" is 0, the processing proceeds to Step 16, in which the CPU 29 sends an OFF signal to the motor driver 30 to stop the motor 26. In the other case, the processing proceeds to Step 17, in which the sign of the count value "count" is determined. When the count value "count" is positive, the processing proceeds to Step 18, while when the count value "count" is negative, the processing proceeds to Step 20.

Specifically, when it is determined that the decrease in rotation amount does not occur, the CPU 29 sets a sum of the control values to be output as a first value corresponding to a sum of the detected rotation amounts. On the other hand, when it is determined that the decrease in rotation amount has occurred, the CPU 29 restricts the amount of decrease in control value per unit time to a value that avoids exceeding the threshold value to output, to the motor driver 30, the control value set so that the sum of the control values becomes larger than the first value.

In this embodiment, the applied voltage of the motor 26 and the moving speed of the head part 22 have the relationship of FIG. 4, and the count value and the applied voltage have the relationship of FIG. 5. The count value is proportional to the rotation speed of the rotational member 8, and hence the applied voltage of the motor 26 is expressed by count×0.5+5 (V). For example, when the count value "count" is 1, the applied voltage is 5.5 V, while when the count value "count" is 14, the applied voltage is 12 V. The maximum applied voltage is 12 V, and hence, when the count value "count" is 14 or larger, the voltage of 12 V is applied.

In Steps 18 and 20, the duty cycle of the PWM is set so that the effective applied voltage of the motor 26 becomes the above-mentioned voltage. The CPU 29 sends an ON/OFF signal according to the duty cycle to the motor driver 30, and in Steps 19 and 21, the CPU 29 sends signals indicating the forward rotation and the reverse rotation to the motor driver 30, respectively.

Figure 7:
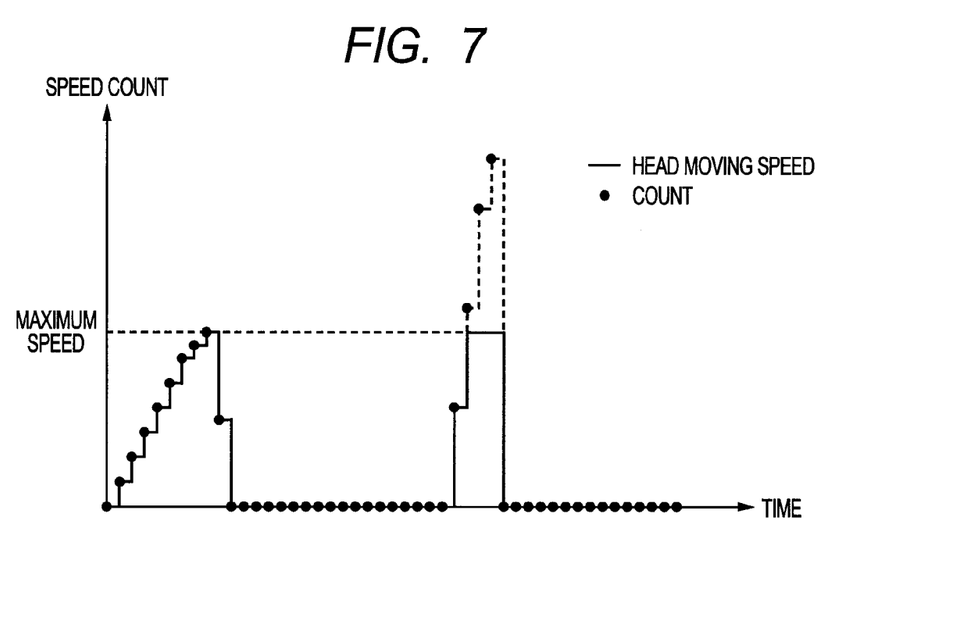
FIG. 7 is an illustration of a relationship between rotation of a conventional joystick and the moving speed of the head part.

Referring to a graph of FIG. 7, a problem arising when the head part 22 is simply driven at a speed proportional to the rotation speed of the rotational member 8 is described. The black spots indicate a plot of counter values of the rotary encoder obtained according to the speeds of the rotational part at the respective samplings, and the solid line indicates the moving speed of the head part 22. The count value and the moving speed have a proportional relationship. The left side of the graph indicates a case where the rotational member 8 has undergone such a rotation operation that the maximum count value becomes the maximum moving speed, and the right side of the graph indicates a case where the speed is doubled and the rotation amount is the same as compared to the rotation operation of the left side. In other words, the right side of the graph corresponds to a case where the rotational member 8 is operated at a rotation speed equal to or higher than the upper limit rotation speed.

In the case of the left side of the graph, the head part 22 is movable at a speed proportional to the count value, while the moving speed of the head part 22 on the right side of the graph is peaked out at the maximum moving speed because of the upper limit of the applied voltage of the motor 26, in a range in which the head part is expected to be moved at a speed indicated by the dotted line. The axis of ordinate represents speed, and the axis of abscissa represents time, which indicates that the area of the solid line portion corresponds to a moving distance. As indicated by the right side of the graph, the moving distance adversely decreases as the rotational part of the joystick is rotated more quickly.

Figure 8:
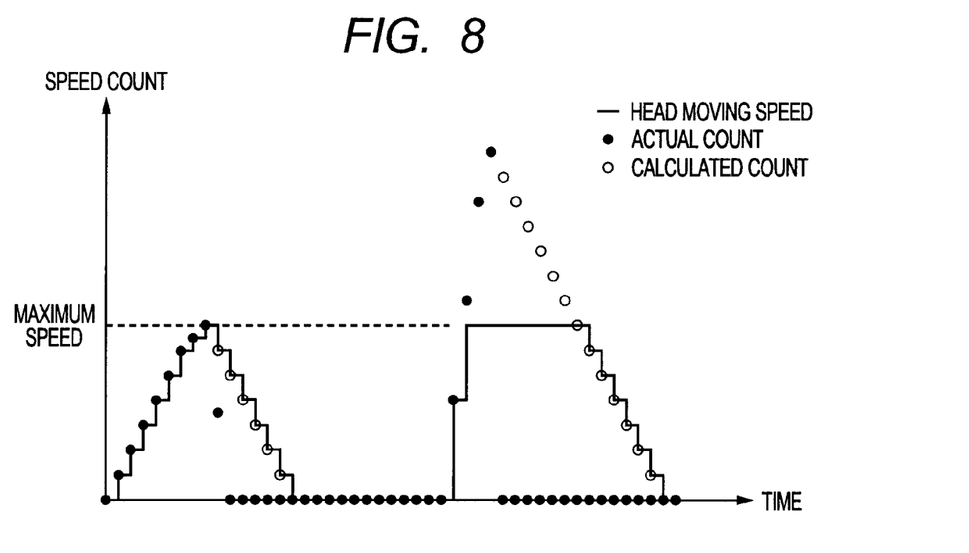
FIG. 8 is an illustration of a relationship between rotation of the joystick and the moving speed of the head part according to the first embodiment.

Referring to a graph of FIG. 8, an operation of this embodiment to be performed in a case where the rotational member 8 has undergone the same rotation operation as that of FIG. 7 is described. The black spots indicate counter values of the rotary encoder 5 obtained according to the speeds of the rotational part at the respective samplings, and the white circles indicate count values calculated in the case where the value obtained by subtracting the predetermined value (in this embodiment, 2) from the count value at the previous sampling is larger than the count value at the current sampling. When the white circle is present, the head part is moved at the speed proportional to the white circle. As a result, unlike the case of FIG. 7, the area of the solid line portion indicating the moving distance becomes larger as the rotational member 8 of the joystick is rotated more quickly as in the case of the left side of the graph.

In other words, as the joystick is rotated more quickly, the head part 22 can be moved more greatly even with the same rotation amount. Further, in a case of fine adjustment, for example, in a case where the count value is 1 or 2, the motor is stopped instantly when the rotation is stopped, and hence the head part 22 is not moved excessively. In a case where the rotation of the joystick is reversed, the voltage is applied to the motor 26 so as to achieve the speed and direction according to the current count value instead of the previous count value, and thus there is no problem with the response.

As described above, as the rotational member 8 of the joystick is rotated more quickly in order to move the head part 22 greatly, the moving amount of the head part 22 becomes larger, and thus operability in the case of rough movement is improved. In the case where the rotational member 8 is rotated slowly for the fine movement, the head part 22 is moved at the speed substantially proportional to the rotation speed, and even when the rotation is reversed, the operation of reversing the rotation is performed instantly. Thus, there is no problem also with the operability of the fine movement.

Specifically, with regard to the rotation speed of the rotational member 8, which is successively detected by the rotary encoder 5 and the up/down counter 28, when the successively detected rotation speed decreases and the amount of decrease in rotation speed is larger than a predetermined threshold value (in an extreme case, when the rotation is stopped), instead of the control value corresponding to the detection value, the control value is restricted so that the value does not exceed the threshold value even though there is a decrease.

If the rotation speed of the rotational member 8 of the joystick is extremely high and the motor 26 is still moving even though the rotational part is stopped, the operator may feel inconvenience. Therefore, when the stopped state of the rotational member 8 continues for a period corresponding to a predetermined number of samplings or more and this fact is detected by the detection means, the previous count value count_pre may be set to 0 to stop the motor 26. Further, in this embodiment, the value obtained by subtracting the predetermined value (fixed value) from the previous count value count_pre is compared to the current count value count_now, but alternatively, as in a case where a value proportional to the previous count value is used for the subtraction instead of the fixed value, the predetermined value may be changed according to the rotation speed detected at the time of sampling.

Second Embodiment

The configuration of this embodiment is the same as that of the first embodiment, but the control method for the motor 26 in the case where the rotational member 8 of the joystick is rotated at high speed is changed from that of the first embodiment.

Similarly to FIGS. 6A and 6B of the first embodiment, a method of solving the problem arising when the head part 22 is simply driven at the speed proportional to the rotation speed of the rotational member 8 is described. A count amount obtained when the speed of vertical movement of the head reaches to an upper limit speed is represented as "max" (corresponding to the upper limit rotation speed described above; in this embodiment, 14).

Figure 9:
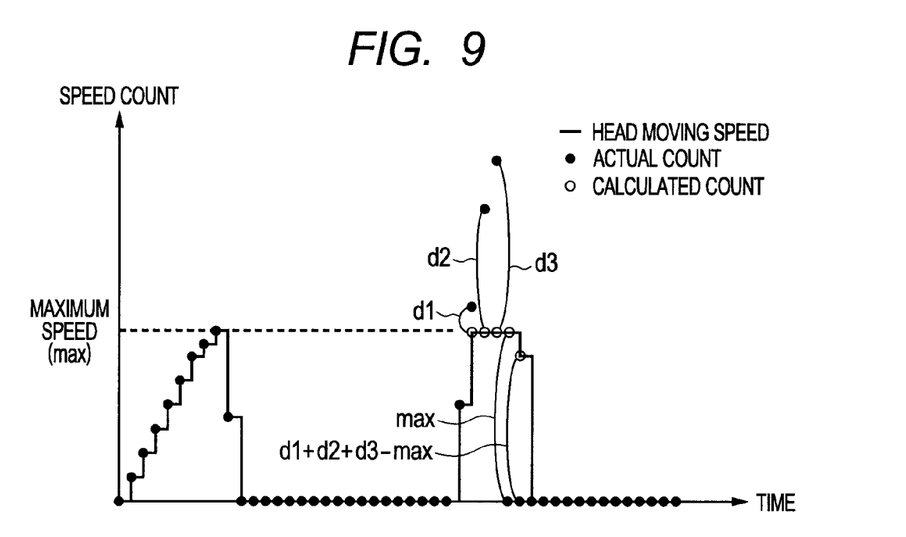
FIG. 9 is an illustration of a relationship between rotation of the joystick and the moving speed of the head part according to a second embodiment of the present invention.

FIG. 9 is an illustration of control of this embodiment. The black spots indicate actual count values and the white circles indicate calculated count values. The left side of the graph indicates a case where the count value does not exceed the value max. When the count value exceeding the value max is detected as in the case of the right side of the graph, a difference between the count value and the value max is calculated by the subtraction means of the CPU 29, and the difference is stored in the storage means of the CPU 29. The differences obtained multiple times during sampling are summed up within the CPU 29 and calculated as a summed speed, which is stored in the storage means. The current count value is set to the value max.

Accordingly, the control of the drive means is executed assuming that the rotation speed obtained at the current sampling is the upper limit rotation speed. Further, in the case indicated by the right side of the graph of FIG. 9, the count value exceeding the value max is input three times, and hence the summed value that is the summed speed is calculated as a value expressed by d1+d2+d3 and is stored in the storage means.

When the count value is below the value max, a difference between the value max and the current count value is compared to the stored summed value, and a smaller value is added to the current count value. The value thus obtained is set as a rotation speed obtained through the current sampling to execute the control of the drive means. Further, the smaller value obtained through the previous comparison is subtracted from the stored summed value by the subtraction means. The same processing is repeated until the summed value becomes 0. Through this processing, as the count value of FIG. 9 for determining the applied voltage of the motor 26, the count value indicated by the white circle is used in a case where the white circle is present, and the count value indicated by the black spot is used in the other case. As a result, the moving speed of the head part 22 proportional to the count value is as indicated by the solid line.

The area of the solid line portion on the left side of the graph equals the area of the solid line portion on the right side, and hence the moving speed of the head part 22 corresponds to the moving speed proportional to the rotation amount irrespective of the rotation speed of the rotational member 8 of the joystick. Thus, the operability can be improved.

Note that, when the stop of the rotational member is detected by the detection means as many times as the predetermined number of samplings or more similarly to the first embodiment, the summed speed used at the previous sampling, that is, the summed speed stored until the previous sampling, may be set to 0 and the above-mentioned processing may be executed. Further, when the rotation direction determined based on the summed speed is different from the rotation direction obtained at the current sampling, the summed speed may be set to 0 to improve the operability.

According to the above-mentioned embodiment, with regard to the rotation speed of the rotational member 8, which is successively detected by the rotary encoder 5 and the up/down counter 28, when the amount of decrease in rotation speed is larger than the predetermined threshold value, the CPU 29 controls the motor driver 30 so that the amount of decrease in rotation speed of the motor 26 according to the decrease in rotation speed is smaller than the amount of decrease in rotation speed that has been detected. With this configuration, even when the rotation speed is greatly increased and then the rotation is not maintained, the amount of decrease in rotation of the motor 26 is suppressed. Accordingly, the adjustment amount of the head part 22 can be increased according to the increase in rotation speed. Further, when the rotational member 8 is rotated so that the amount of decrease in rotation speed becomes sufficiently small, the motor 26 can be rotated according to the rotation speed of the rotational member 8, and thus fine adjustment of the head part 22 is possible.

In the above-mentioned embodiments, the present invention is applied to the control of rotating the rotational dial of the joystick, but the present invention is not limited thereto. The present invention is also applicable to an electrically-driven joystick, in which the joystick itself is rotated.

Note that, the above-mentioned embodiments have described the example in which the present invention is applied to the joystick for controlling the ophthalmologic apparatus, but the control target is not limited to the ophthalmologic apparatus. For example, the control target may be an apparatus including an arbitrary drive part, or a display control part for displaying a specific image object on a display part. In those cases, the drive part is driven according to a control value output from a control part of the joystick, or a display format such as a position and a size of the displayed image object is changed. Accordingly, the rotation amount described in the above-mentioned embodiments is handled as a drive amount. Here, the control part of the joystick is constituted by a CPU for receiving information on the rotation speed (rotation amount per unit time) and the rotation direction detected by the rotary encoder and the up/down counter, and outputting the control value. The processing of the present invention can be implemented in such a manner that the CPU sequentially loads, on a ROM, programs for performing the same control as that of the above-mentioned embodiments and executes the programs thus loaded.

As described above, through the above-mentioned control, the adjustment amount can be increased according to the rotation speed, and fine adjustment is also possible even without a high-performance motor.

In particular, in the ophthalmologic apparatus, an operation system including the joystick and the rotational member is conventionally widely used. By applying the present invention to the rotational member, the labor of the operation involved in the adjustment necessitating a large adjustment amount can be reduced, and fine adjustment can also be performed with no change of the conventional apparatus and operability. Accordingly, the user can easily adjust the ophthalmologic apparatus, enabling efficient eye diagnosis.

Other Embodiments

Further, the present invention is also implemented by executing the following processing. Specifically, in this processing, software (program) for implementing the functions of the above-mentioned embodiments is supplied to a system or an apparatus via a network or various kinds of storage medium, and a computer (or CPU, MPU, etc.) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-194641, filed Aug. 31, 2010, which is hereby incorporated by reference herein in its entirety.

What is claimed is:

1. A control apparatus for controlling a control target, the control apparatus comprising:
   a rotational member;
   a detection unit for repeatedly detecting a rotation amount of the rotational member; and
   a control unit for outputting a control value which corresponds to the rotation amount detected by the detection unit and which is used for controlling the control target,
   wherein when there has occurred a decrease in the rotation amount such that an amount of decrease per unit time in the control value exceeds a threshold value, the control unit restricts the amount of decrease per unit time in the control value to a restricted control value that avoids exceeding the threshold value, and outputs the restricted control value.

2. An ophthalmologic apparatus, comprising:
   the apparatus according to claim 1; and
   an optical unit that is the control target.

3. A control apparatus according to claim 1, wherein when a stop of the rotational member is detected by the detection unit as many times as a predetermined number of samplings or more, the control unit sets a rotation speed of the rotational member at a previous sampling to zero.

4. A control apparatus according to claim 1, wherein the control unit changes a predetermined value subtracted from a rotation speed at a previous sampling according to the rotation speed at the previous sampling.

5. A control apparatus according to claim 1, wherein when a stop of the rotational member is detected by the detection unit as many times as a predetermined number of samplings or more, the control unit sets a summed speed used at a previous sampling to zero.

6. A control apparatus according to claim 1, wherein when a rotation direction determined based on a summed speed is different from a rotation direction at a current sampling, the control unit sets the summed speed to zero.

7. A control apparatus according to claim 1, further comprising:
   a storage unit for storing a rotation speed and a rotation direction of the rotational member that are detected by the detection unit; and
   a subtraction unit for calculating, when the rotation direction at a previous sampling that is stored in the storage unit and the rotation direction at a current sampling are the same, or when the rotation speed is zero, a rotation speed obtained by subtracting a predetermined value from the rotation speed at the previous sampling that is stored in the storage unit.

8. A control apparatus according to claim 1, further comprising:
   a storage unit for storing a rotation speed and a rotation direction of the rotational member that are detected by the detection unit, and further storing an upper limit rotation speed corresponding to an upper limit of a rotation speed of a drive unit, and a difference between the upper limit rotation speed and the rotation speed in a case where the detected rotation speed of the rotational member exceeds the upper limit rotation speed; and
   a subtraction unit for subtracting the upper limit rotation speed from the rotation speed to calculate the difference.

9. A control method for an apparatus including a rotational member for controlling a control target, the control method comprising:
   repeatedly detecting a rotation amount of the rotational member;
   outputting a control value which corresponds to the rotation amount detected by the detecting and which is used for controlling the control target;
   determining whether or not there has occurred a decrease in the rotation amount such that an amount of decrease per unit time in the control value exceeds a threshold value;
   outputting, when it is determined that the decrease in the rotation amount does not occur, the control value so that a sum of control values to be output becomes a first value which corresponds to a sum of the detected rotation amounts; and
   restricting, when it is determined that the decrease in the rotation amount has occurred, the amount of decrease per unit time in the control value to a restricted control value that avoids exceeding the threshold value, and outputting the restricted control value so that a sum of control values to be output becomes larger than the first value.

10. A non-transitory tangible medium having recorded thereon a program for causing a computer to perform steps of the control method according to claim 9.

11. An ophthalmologic apparatus, comprising:
    a detection unit for detecting a rotation speed and a rotation direction of a rotational member at predetermined sampling intervals;
    a drive unit for electrically performing vertical movement of an optical system for imaging, observation, and measurement of an eye to be inspected;
    a control unit for controlling the drive unit at a speed and in a direction respectively corresponding to the rotation speed and the rotation direction of the rotational member that are detected at a current sampling by the detection unit;
    a storage unit for storing the rotation speed and the rotation direction of the rotational member that are detected by the detection unit; and
    a subtraction unit for calculating, when the rotation direction at a previous sampling that is stored in the storage unit and the rotation direction at the current sampling are the same, or when the rotation speed is zero, a rotation speed obtained by subtracting a predetermined value from the rotation speed at the previous sampling that is stored in the storage unit,
    wherein the control unit compares the rotation speed obtained through the subtraction to the rotation speed at the current sampling, and sets a higher speed as the rotation speed at the current sampling to be used for controlling the drive unit.

12. An ophthalmologic apparatus, comprising:
    a detection unit for detecting a rotation speed and a rotation direction of a rotational member at predetermined sampling intervals;
    a drive unit for electrically performing vertical movement of an optical system for imaging, observation, and measurement of an eye to be inspected;
    a control unit for controlling the drive unit at a speed and in a direction respectively corresponding to the rotation speed and the rotation direction of the rotational member that are detected at a current sampling by the detection unit;

a storage unit for storing the rotation speed and the rotation direction of the rotational member that are detected by the detection unit, and further storing an upper limit rotation speed corresponding to an upper limit of a rotation speed of the drive unit, and a difference between the upper limit rotation speed and the rotation speed in a case where the detected rotation speed of the rotational member exceeds the upper limit rotation speed; and a subtraction unit for subtracting the upper limit rotation speed from the rotation speed to calculate the difference, wherein when a current rotation speed of the rotational member exceeds the upper limit rotation speed, the control unit sums up the differences stored in the storage unit to calculate a summed speed, which is stored in the storage unit, and sets the upper limit rotation speed as the current rotation speed to be used for controlling the drive unit, and wherein when the rotation speed is lower than the upper limit rotation speed, the control unit compares the summed speed to a current difference obtained by subtracting the current rotation speed from the upper limit rotation speed stored in the storage unit, subtracts a lower rotation speed from the summed speed to obtain a new summed speed, which is stored in the storage unit, and sets a speed obtained by adding the lower rotation speed to the current rotation speed, as the current rotation speed to be used for controlling the drive unit.

13. An ophthalmologic apparatus, comprising:
detection means for detecting a rotation speed and a rotation direction of a rotational member at predetermined sampling intervals;
drive means for electrically performing vertical movement of an optical system for imaging, observation, and measurement of an eye to be inspected;
control means for controlling the drive means at a speed and in a direction respectively corresponding to the rotation speed and the rotation direction of the rotational member that are detected at a current sampling by the detection means;
storage means for storing the rotation speed and the rotation direction of the rotational member that are detected by the detection means; and
subtraction means for calculating, when the rotation direction at a previous sampling that is stored in the storage means and the rotation direction at the current sampling are the same, or when the rotation speed is zero, a rotation speed obtained by subtracting a predetermined value from the rotation speed at the previous sampling that is stored in the storage means,
wherein the control means compares the rotation speed obtained through the subtraction to the rotation speed at the current sampling, and sets a higher speed as the rotation speed at the current sampling to be used for controlling the drive means.

14. A control method for an ophthalmologic apparatus, comprising:
detecting by detection means, a rotation speed and a rotation direction of a rotational member at predetermined sampling intervals;
controlling a drive means which electrically performs vertical movement of an optical system for imaging, observation, and measurement of an eye to be inspected, at a speed and in a direction respectively corresponding to the rotation speed and the rotation direction of the rotational member that are detected at a current sampling by the detection means;
storing by a storage unit, the rotation speed and the rotation direction of the rotational member that are detected by the detection means; and
calculating, when the rotation direction at a previous sampling that is stored by the storage unit and the rotation direction at the current sampling are the same, or when the rotation speed is zero, a rotation speed obtained by subtracting a predetermined value from the rotation speed at the previous sampling that is stored by the storage unit,
wherein the rotation speed obtained through the subtraction is compared to the rotation speed at the current sampling, and is set a higher speed as the rotation speed at the current sampling to be used for controlling the drive means.

15. A non-transitory tangible medium having recorded thereon a program for causing a computer to perform steps of the control method according to claim 14.

16. A control method for an ophthalmologic apparatus, comprising:
detecting by a detection unit, a rotation speed and a rotation direction of a rotational member at predetermined sampling intervals;
controlling a drive unit which electrically performs vertical movement of an optical system for imaging, observation, and measurement of an eye to be inspected, at a speed and in a direction respectively corresponding to the rotation speed and the rotation direction of the rotational member that are detected at a current sampling by the detection unit;
storing in a storage unit, the rotation speed and the rotation direction of the rotational member that are detected by the detection unit; and
calculating, when the rotation direction at a previous sampling that is stored in the storage unit and the rotation direction at the current sampling are the same, or when the rotation speed is zero, a rotation speed obtained by subtracting a predetermined value from the rotation speed at the previous sampling that is stored in the storage unit,
wherein the rotation speed obtained through the subtraction is compared to the rotation speed at the current sampling, and is set a higher speed as the rotation speed at the current sampling to be used for controlling the drive unit.

17. A non-transitory tangible medium having recorded thereon a program for causing a computer to perform steps of the control method according to claim 16.

18. A control method for an ophthalmologic apparatus, comprising:
detecting by a detection unit, a rotation speed and a rotation direction of a rotational member at predetermined sampling intervals;
controlling a drive unit which electrically performs vertical movement of an optical system for imaging, observation, and measurement of an eye to be inspected, at a speed and in a direction respectively corresponding to the rotation speed and the rotation direction of the rotational member that are detected at a current sampling by the detection unit;
storing by a storage unit, the rotation speed and the rotation direction of the rotational member that are detected by the detection unit, and further storing an upper limit rotation speed corresponding to an upper limit of a rotation speed of the drive unit, and a difference between the upper limit rotation speed and the rotation speed in a case where the detected rotation speed of the rotational member exceeds the upper limit rotation speed; and subtracting the upper limit rotation speed from the rotation speed to calculate the difference, wherein when a current rotation speed of the rotational member exceeds the upper limit rotation speed, the differences stored in the storage unit is summed up to calculate a summed speed, which is stored in the storage unit, and sets the upper limit rotation speed as the current rotation speed to be used for controlling the drive unit, and wherein when the rotation speed is lower than the upper limit rotation speed, the summed speed is compared to a current difference obtained by subtracting the current rotation speed from the upper limit rotation speed stored in the storage unit, a lower rotation speed is subtracted from the summed speed to obtain a new summed speed, which is stored in the storage unit, and a speed obtained by adding the lower rotation speed to the current rotation speed, is set as the current rotation speed to be used for controlling the drive unit.

19. A non-transitory tangible medium having recorded thereon a program for causing a computer to perform steps of the control method according to claim 18.

* * * * *